United States Patent

Iyer et al.

[11] Patent Number: 5,996,413
[45] Date of Patent: Dec. 7, 1999

[54] METHOD FOR TESTING A PRESTRESSED CONCRETE CONDUIT

[75] Inventors: Subramanian T. M. Iyer, Brea; Harvey O. Webster, III, Rancho Cucamonga, both of Calif.

[73] Assignee: The Metropolitan Water District of Southern California, La Verne, Calif.

[21] Appl. No.: 08/962,438

[22] Filed: Oct. 31, 1997

[51] Int. Cl.$^6$ .......................... G01N 29/04; G01N 29/18; G01N 29/20
[52] U.S. Cl. .................. 73/592; 73/598; 73/600
[58] Field of Search .............. 73/594, 598, 600, 73/579, 584, 635, 637, 592

[56] References Cited

U.S. PATENT DOCUMENTS

| | | | |
|---|---|---|---|
| 2,667,068 | 1/1954 | Viehe et al. . | |
| 4,122,723 | 10/1978 | Levizzari et al. . | |
| 4,163,393 | 8/1979 | Gutierrez et al. | 73/584 |
| 4,166,393 | 9/1979 | Linder et al. . | |
| 4,212,205 | 7/1980 | West et al. . | |
| 4,331,034 | 5/1982 | Takeda et al. | 73/637 |
| 4,429,575 | 2/1984 | Akishika | 73/584 |
| 4,522,063 | 6/1985 | Ver Nooy . | |
| 4,539,847 | 9/1985 | Paap . | |
| 4,843,384 | 6/1989 | House et al. | 73/637 |
| 5,333,501 | 8/1994 | Okada et al. . | |
| 5,404,755 | 4/1995 | Olson et al. | 73/584 |
| 5,526,690 | 6/1996 | Louie et al. | 73/592 |
| 5,540,096 | 7/1996 | Woodcock et al. . | |
| 5,612,495 | 3/1997 | Shimada et al. . | |

FOREIGN PATENT DOCUMENTS 0147642  9/1983  Japan .
0293151  12/1987  Japan .

*Primary Examiner*—Hezron Williams
*Assistant Examiner*—Nashmiya Fayyaz
*Attorney, Agent, or Firm*—Sheldon & Mak; Denton L. Anderson

[57] ABSTRACT

A method is provided for testing prestressed concrete pipe. In the method, elastic waves are serially induced at at least three different inducing locations along the surface of the conduit. The shear wave component of each induced elastic wave is detected by at least one, and preferably two, acoustic sensors disposed at fixed sensing sites along the conduit. The relationship between at least one parameter of each induced shear wave and the distance between each inducing location and the acoustic sensor(s), are correlated and compared with standard correlations to identify structural discontinuities in the conduit. In a typical example of the method, elastic waves are induced using a mechanical hammer at multiple inducing sites around a multiplicity of annuli along the length of the conduit. Each annulus is separated from adjoining annuli by 2–4 feet.

39 Claims, 5 Drawing Sheets

METHOD FOR TESTING A PRESTRESSED CONCRETE CONDUIT

FIELD OF THE INVENTION

This invention relates generally to methods for testing prestressed concrete conduits, and specifically to methods for testing prestressed concrete conduits using acoustic sensors.

BACKGROUND

Prestressed concrete pipe is very commonly used to carry large quantities of bulk liquid, such as potable water, under pressures of typically 150 psig to 300 psig. In a typical example of prestressed concrete conduit, round concrete pipe having a wall thickness of between about 10 inches and about 20 inches is tightly wrapped with prestressing wire having a thickness between about 0.16 inches and 0.35 inches. The prestressing wire is typically then covered with mortar to minimize corrosion of the wire. Such prestressed concrete pipes can conveniently be used below ground.

A serious problem regarding the use of prestressed concrete pipe is the danger of the pipe exploding after a portion of the prestressing wire fails for one reason or another. In such an explosion, it is not unusual for large chunks of concrete to be thrown many hundreds of feet. Such failures are, therefore, very dangerous.

The testing of prestressed concrete pipe is difficult to do in a nondestructive manner. This is because the prestressing wire is thoroughly covered with mortar. Until recently, there has been no accurate method of non-destructive testing of prestressed concrete pipe.

The Washington Suburban Sanitary Commission has attempted to provide a non-destructing method for testing prestressed concrete pipe. The Washington Suburban Sanitary Commission method is set forth in U.S. Pat. No. 5,540,096, the contents of which are incorporated herein by reference. In the Washington Suburban Sanitary Commission method, sound waves are imparted to one side of the concrete pipe and sensed by a single acoustic sensor disposed immediately adjacent the inducing site. One or more parameters of the acoustic wave detected by the acoustic sensor is then correlated with standards to identify discontinuities.

The problem with this method is that it detects discontinuities only at a single point proximate to the acoustic wave induction site. The method is not capable of detecting discontinuities away from the acoustic wave induction site. Accordingly, the method is exceedingly time-consuming and expensive because literally hundreds, if not thousands, of readings have to be taken to cover the entire surface of even a 20-foot section of prestressed concrete pipe.

Accordingly, there is a need for a method whereby prestressed concrete pipe can be simply, inexpensively and quickly tested.

SUMMARY

The invention satisfies these needs. The invention is a method for testing a prestressed concrete conduit wherein the conduit comprises a hollow concrete body tightly wrapped with a prestressing wire. The method comprises the steps of (a) serially inducing an elastic wave having a shear wave component into the conduit at at least three different inducing locations along the surface of the conduit; (b) sensing each shear wave component induced at each of the inducing locations with at least one acoustic sensor disposed at a first fixed sensing site proximate to the conduit; (c) correlating the relationship between (i) at least one parameter of each shear wave component induced at each inducing location and sensed by the acoustic sensor, and (ii) and the distance between the inducing location and the acoustic sensor; and (d) comparing the correlations produced in step (c) with a standard correlation to identify structural discontinuities in the conduit.

In a typical application of the method, a pair of acoustic sensors are used, one at each of two fixed sensing sites at opposite ends of the conduit, and the elastic wave is induced into the concrete body by use of a mechanical hammer which imparts a constant force on each stroke.

Preferably, the elastic wave is induced at inducing locations located about an annular section of the conduit perpendicular to the length of the conduit. In one variation of the method, three inducing locations along each annulus are used, each inducing location being disposed at 120° intervals around the annulus. Typically, inducing locations are chosen along annuli disposed about every three or four feet along the length of the conduit.

Preferably, several parameters of each shear wave are correlated using typical acoustic emission equipment. The resulting data is then reviewed for anomalies which would indicate structural discontinuities in the conduit.

The method has been found to provide an inexpensive, non-destructive method of rapidly and accurately testing prestressed concrete conduits.

DRAWINGS

These features, aspects and advantages of the present invention will become better understood with regard to the following description, appended claims and accompanying figures where:

DETAILED DESCRIPTION

Figure 1:
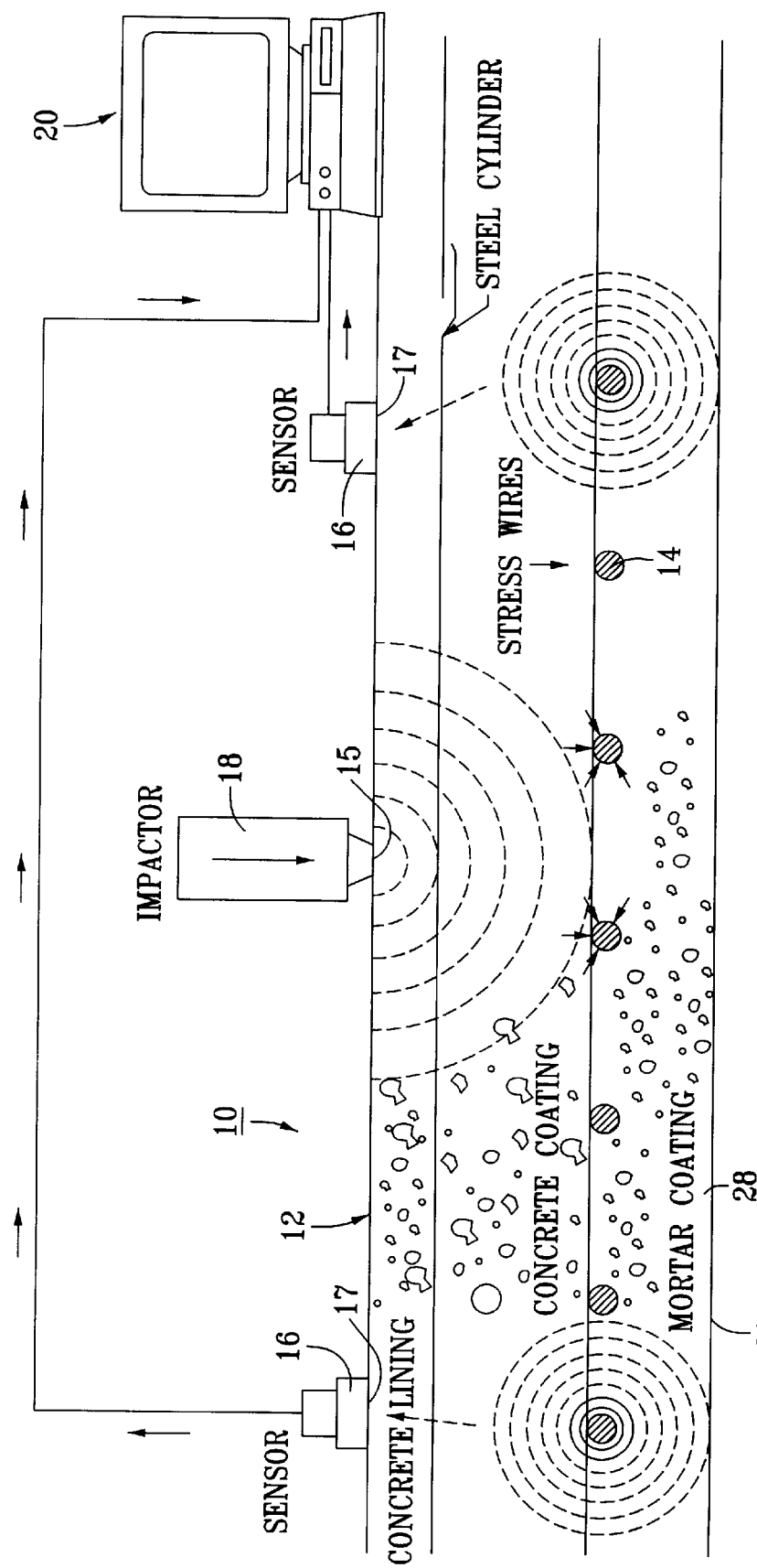
FIG. 1 is a diagrammatic rendition of equipment useful in practicing the method of the invention.

The following discussion describes in detail one embodiment of the invention and several variations of that embodiment. This discussion should not be construed, however, as limiting the invention to those particular embodiments. Practitioners skilled in the art will recognize numerous other embodiments as well.

The invention is a method for testing a prestressed concrete conduit 10 wherein the prestressed concrete conduit comprises a hollow concrete body 12 tightly wrapped with a prestressing wire 14. The method comprises the steps of (a) serially inducing an elastic wave having a shear wave component into the conduit 10 at at least three different inducing locations 15 along the surface of the conduit 10; (b) sensing each shear wave component induced at each of the inducing locations 15 with at least one acoustic sensor 16 disposed at a first fixed sensing site 17 proximate to the conduit 10; (c) correlating the relationship between (i) at least one parameter of each shear wave component induced at each inducing location 15 and sensed by the acoustic sensor 16, and (ii) and the distance between the inducing location 15 and the acoustic sensor 16; and (d) comparing the correlations produced in step (c) with a standard correlation to identify structural discontinuities in the conduit 10.

Figure 2:
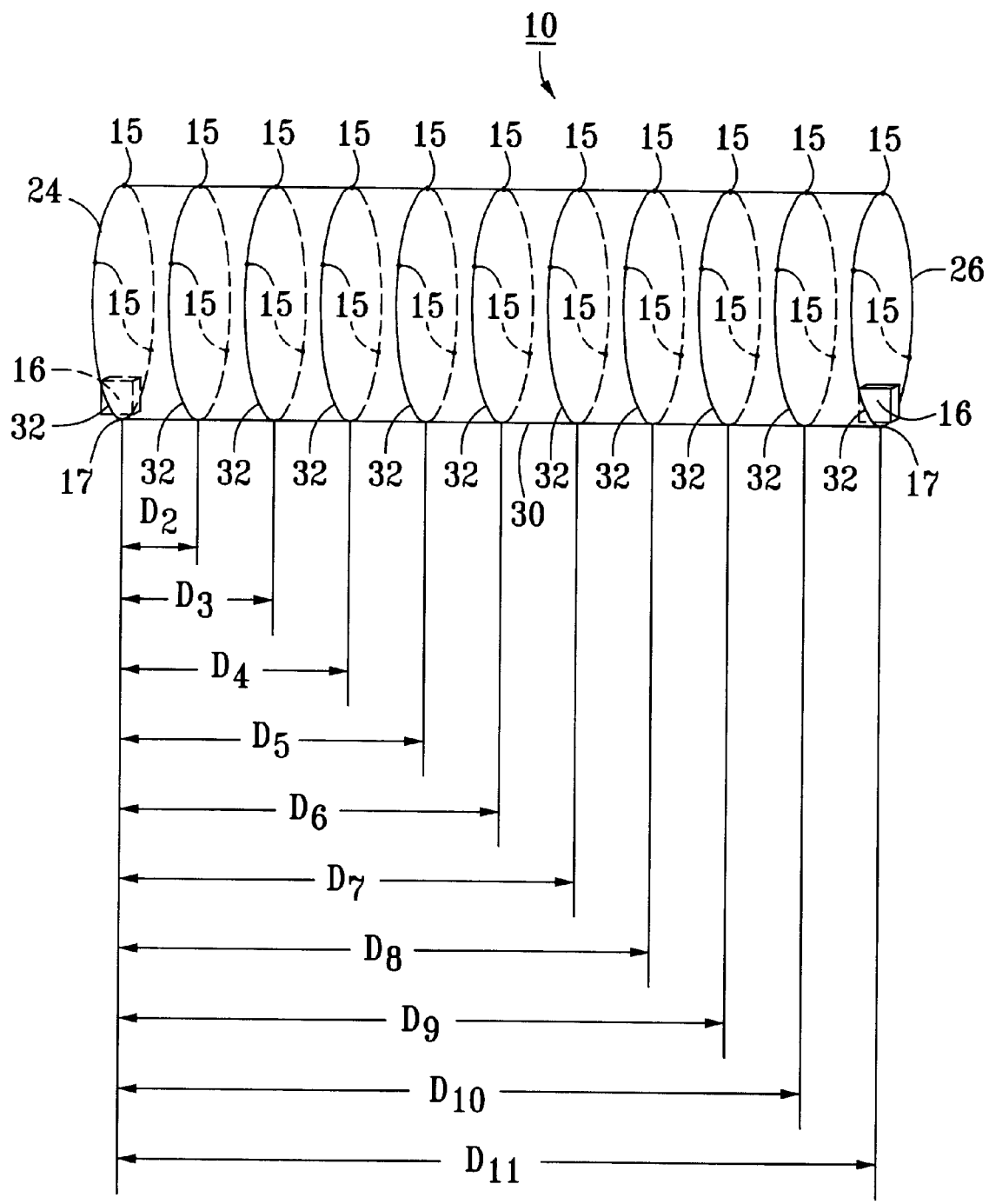
FIG. 2 is a diagrammatic perspective view of a concrete section illustrating how the concrete section is tested by a method incorporating features of the invention.

The invention is conveniently used to test sections of prestressed concrete pipe, such as shown in FIGS. 1 and 2. Such prestressed concrete pipe typically comes in lengths of 20 to 40 feet. Such pipe typically has an internal diameter between about 48 inches and about 220 inches.

The concrete body 12 is typically between about 10 inches and about 20 inches thick.

The prestressing wire 14 is typically steel and varies in thickness between about 0.162 inches and 0.312 inches. Minimal tensile strength is typically between about 150 and about 300 ksi, based on the pressure rating of the pipe section.

The step of serially inducing elastic waves into the conduit 10 can be accomplished by suitable elastic wave inducing equipment 18. Preferably, such equipment 18 is capable of repeatedly imparting elastic waves of approximately equal characteristics. This facilitates the evaluation and correlation of the resulting data. Mechanically operated hammers and other mechanical impact devices can be used. In one embodiment, a "Schmidt hammer," such as the device manufactured by James Instruments, Inc., of Chicago, Ill., known as the "H-Meter," can conveniently and inexpensively be used. Such an instrument typically imparts about 2.2 joules of energy on each cycle. In a "Schmidt hammer," a spring loaded hammer head is capable of repeatedly delivering a mechanical impact of approximately equal energies.

The acoustic sensors 16 are typically piezoelectric acoustic sensors. A typical acoustic sensor 16 is a piezoelectric acoustic sensor having a frequency range of between about 5 khz and 150 khz. Preferably, the acoustic sensor is sensitive in the 5–30 khz range. Acoustic sensors 16 useful in the method of the invention include Models R3I (30 khz), R151 (150 khz) and R1.51 (15 khz), sold by Physical Acoustics Corp. of Lawenceville, N.J.

Figure 3:
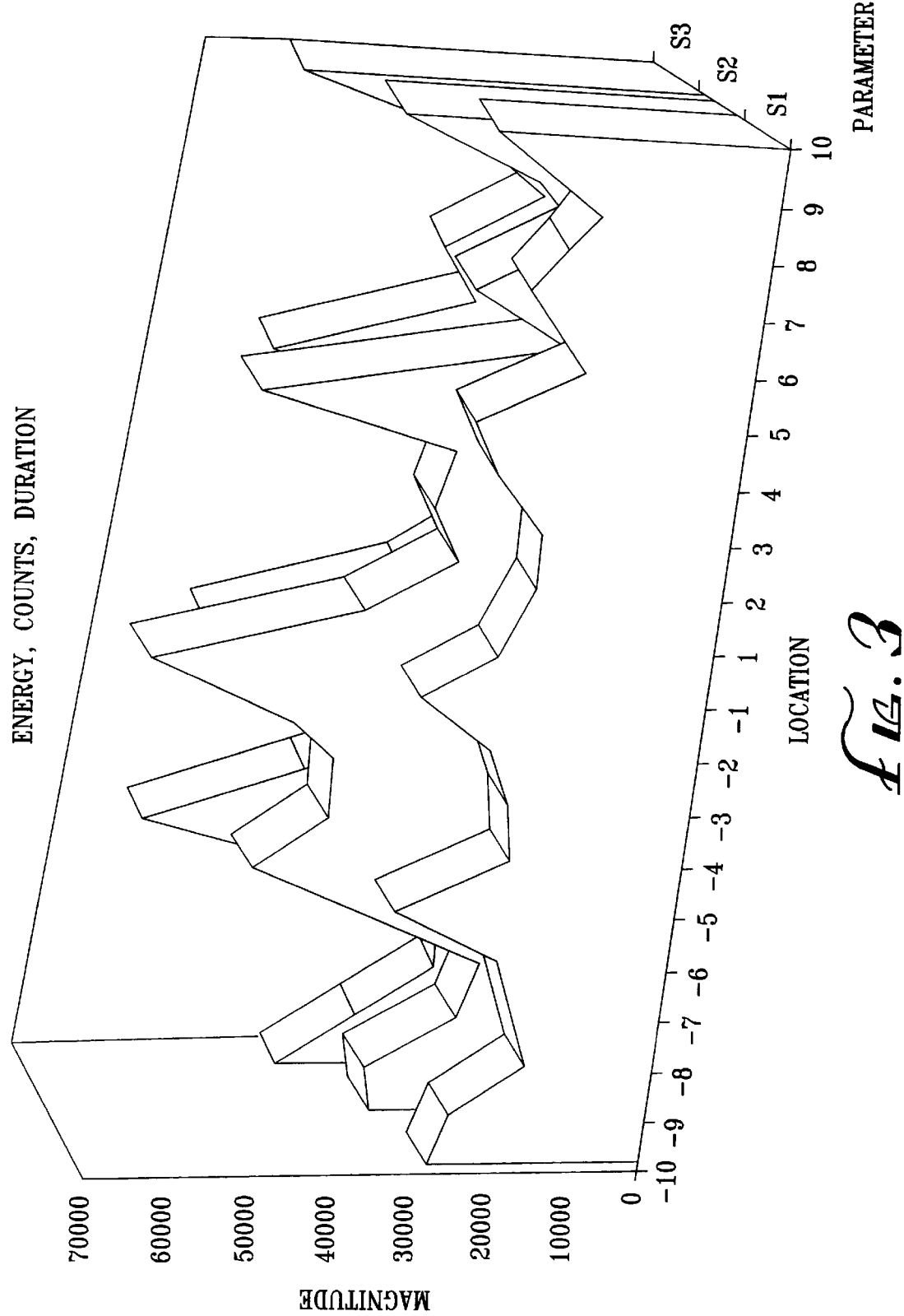
FIG. 3 is a graphical depiction of a typical data output resulting from the testing of a prestressed concrete conduit using the method of the invention.
Figure 4:
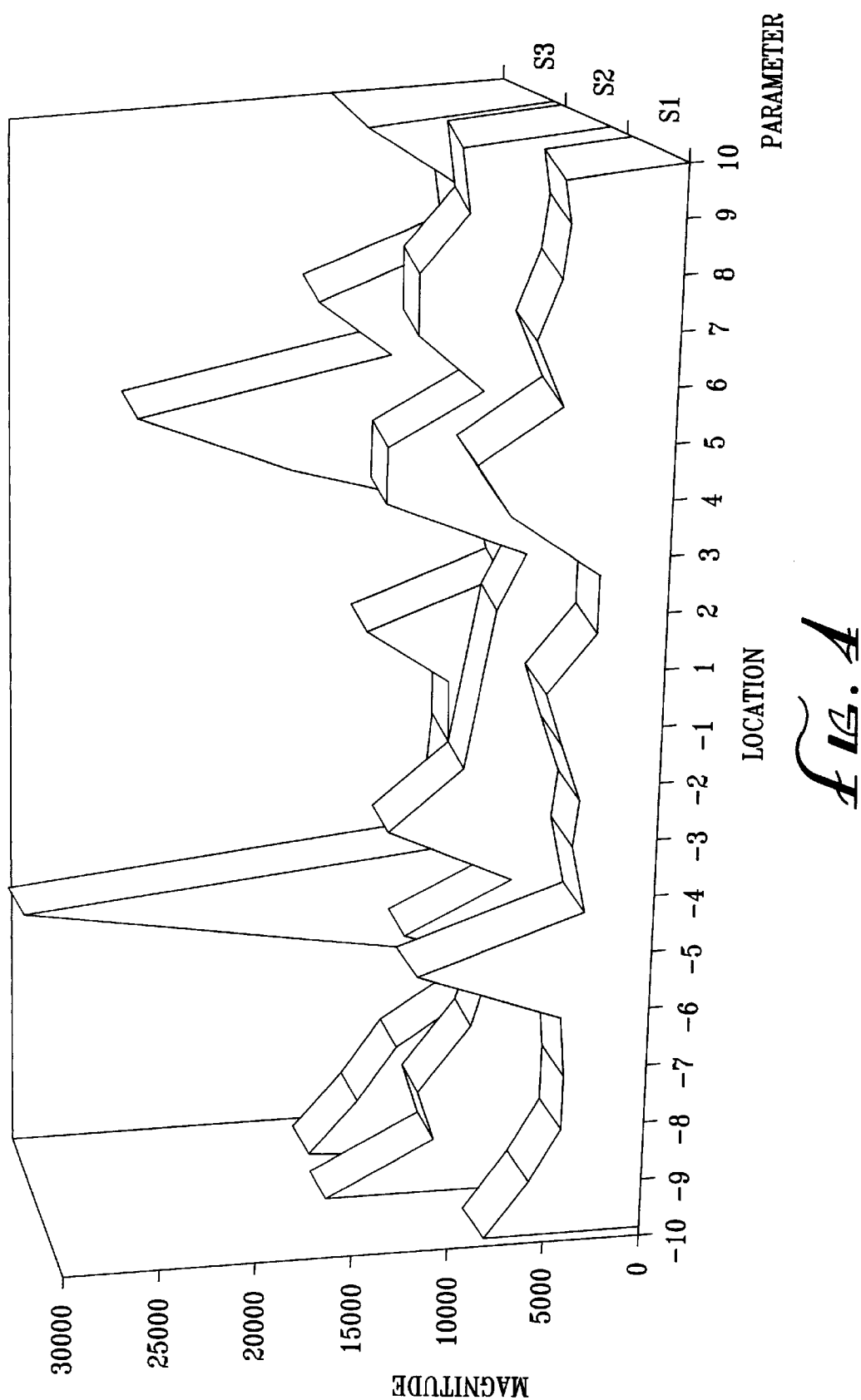
FIG. 4 is a graphical depiction of additional typical data output resulting from the testing of the prestressed concrete conduit referenced above regarding FIG. 3 using the method of the invention.

Software and hardware 20 useful in such computer-assisted correlations are available within the industry. Suitable acoustic emission software, such as those sold by Physical Acoustics of Lawrenceville, N.J., under the name MISTRAS, can be conveniently used. Such software typically is capable of receiving signals from the acoustic sensors 16, digitizing such signals and displaying data from the signals in a variety of convenient forms, including graphical representations, such as shown in FIGS. 3 and 4.

The concrete conduit 10 can be a continuous length of conduit. More typically, the concrete conduit 10 is a concrete conduit section 22 having a length between about 20 feet and about 40 feet. Such conduit sections 22 can be connected end to end, however, to form a continuous run of conduit 10. Preferably in such configurations, each separate conduit section 22 is tested separately because of test data anomalies which tend to exist at the interface between sections 22.

The concrete body 12 typically has a first end 24 and a second end 26. In a typical application of the method of the invention, two acoustic sensors 16 are used, the first disposed at a sensing site 17 proximate to the first end 24 of the concrete body 12 and the second proximate to the second end 26 of the concrete body 12. Typically, the acoustic sensors 16 are physically attached to the surface of the concrete body 12 using an acoustic couplant disposed between the sensor 16 and the surface of the conduit 10 to act as an acoustic transmitting medium. A typical acoustic couplant is Ultragel II, sold by Sonotech, Inc., of Billingham, Wash. Where the concrete conduit 10 is used to transport potable water, a glycerol-based couplant, such as Ultragel II, is preferred because of its non-water polluting characteristics.

The prestressing wire 14 is typically covered with a filler material 28, such as mortar, to form an exterior wall 30. The acoustic sensors 16 can be disposed proximate to either the interior wall of the concrete conduit 10 or the exterior wall 30.

The shear wave is typically induced at a plurality of inducing locations 15 spaced apart, typically evenly, between the first acoustic sensor 16 and the second acoustic sensor 16. In a typical variation of the method of the invention, inducing locations 15 are disposed at at least three different distances, $d_1$, $d_2$ and $d_3$, from the first end of the concrete body. At each of these different distances, it is typical that two or more inducing locations 15 are chosen about an annular surface ring 32 defined by the distance $d_1$ from the first end of the concrete body. In one preferred embodiment, three inducing locations 15 are chosen about each annulus 32. Each inducing location 15 about the annulus 32 is typically equidistant from adjoining inducing locations 15 on the annulus 32. Thus, where three inducing locations 15 are chosen at any particular annulus 32, the inducing locations 15 are generally disposed spaced-apart by an arc of about 120°.

In a typical application of the method, inducing location annuli 32 are chosen along the length of the concrete body, spaced-apart by substantially equal distances, each between about 2 feet and about 4 feet, typically about 3 feet.

Accordingly, in the typical testing of a 30 foot length of prestressed concrete conduit 10 as illustrated in FIG. 2, two acoustic sensors 16 are disposed at opposite ends of the conduit 10, either on the external wall 30 or on the internal wall. Eleven inducing location annuli 32 are located along the length of the concrete body 12, beginning at the first end 24 of the concrete body and ending at the second end 26 of the concrete body. Thus, the eleven inducing location annuli 32 are located at $d_1$=the distance of each annulus 32 from the first end of: $d_1$=0 feet from the first end of the concrete body 12, $d_2$=3 feet, $d_3$=6 feet, $d_4$=9 feet, $d_5$=12 feet, $d_6$=15 feet, $d_7$=18 feet, $d_8$=21 feet, $d_9$=24 feet, $d_{10}$=27 feet and $d_{11}$=30 feet. At each inducing location annulus 32 at least three different inducing locations 15 are preferably located, each separated from adjoining inducing locations 15 on the annulus 32 by an arc of about 120°. Accordingly, in this example, 33 inducing locations 15 are used.

In the method of the invention, it is typical to induce elastic waves at each inducing location 15 one time. However, inducing elastic waves at each inducing location 15 a plurality of times can also be practiced so as to better recognize and discard anomalous data.

A crew of two to three men can completely and adequately test a 30-foot section 22 of prestressed concrete conduit 10 in less than about 30 minutes.

Figure 5:
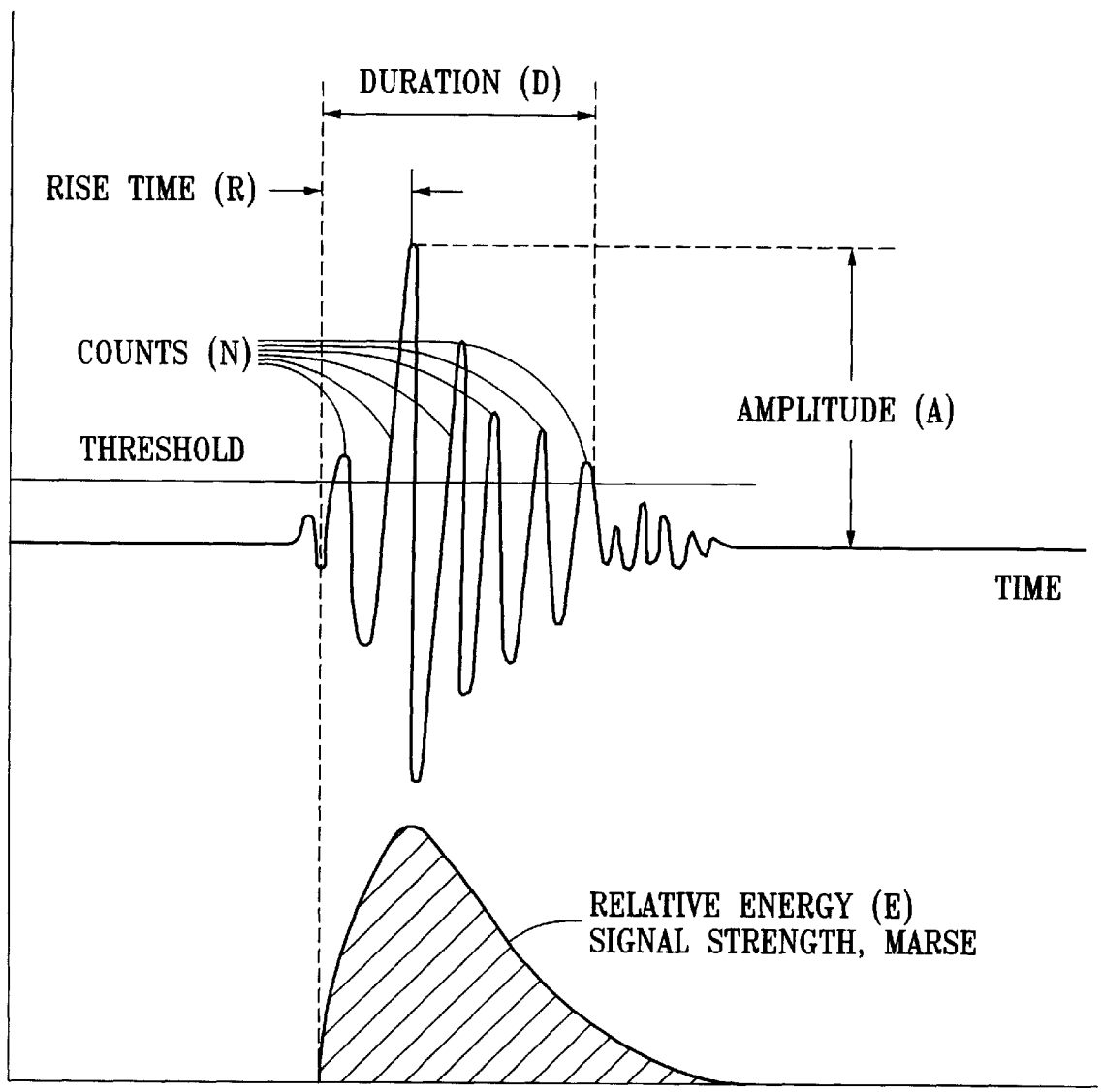
FIG. 5 is a graphical depiction of several acoustic emission signal features useable in the invention.

The parameter of the shear wave components correlated in Step (c) of the method can be any of several of the many conveniently identified parameters of a shear wave, including total energy, amplitude, frequency, counts above a predetermined threshold, duration, average frequency, rise time, velocity and counts to peak. FIG. 5 illustrates these several parameters. Total energy is the total area within the curve defined by the time/waveform relationship. Amplitude means peak amplitude. Frequency is the number of fluctuations of the curve per unit time. Counts above a predetermined threshold is the number of times that the curve rises above a predetermined threshold amplitude. Duration is the time that the curve oscillates on both sides of a predetermined threshold amplitude. Average frequency is counts to peak divided by rise time. Rise time is the time between the first moment that the curve rises above a predetermined threshold amplitude and the time the curve reaches its peak amplitude. Velocity is the frequency of the wave times the wave length. Counts to peak is the number of times the curve oscillates above a predetermined threshold amplitude until the curve reaches its peak amplitude.

In all cases, the predetermined threshold amplitude is generally chosen to be higher than the background noise existing at the testing site. Accordingly, the parameters defined by the threshold amplitude effectively eliminate any chance from error arising from background noise. The background noise level existing at the test site is easily determined by installing the acoustic sensors 16 at the sensing site and noting the amplitude of the background noise prior to any intentional inducement of elastic wave energy into the conduit 10 pursuant to the method of the invention.

In a typical application of the method, more than one parameter of the shear wave component are correlated. Where two or more parameters are correlated, the most common two are (i) total energy and peak amplitude, (ii) peak amplitude and average frequency, (ii) peak amplitude and counts, and (iv) velocity and frequency. Where three or more parameters are correlated, the most commonly used parameters are (i) energy, amplitude and counts, (ii) energy, average frequency and counts, (iii) peak amplitude, average frequency and counts, and (iv) peak amplitude, velocity and frequency.

EXAMPLE

A section of concrete pipe was integrity-tested using the method of the invention. The concrete pipe section was 20 feet long and had an inside diameter of 58.5 inches.

Two acoustic sensors were attached to the inside surface of the concrete pipe at opposite ends of the pipe. Both acoustic sensors were disposed at the lowest elevation within the pipe (the "6 o'clock" position). Each acoustic sensor was a Model No. R31 (30 khz), manufactured by Physical Acoustics Corp. of Lawrenceville, N.J.

Shear waves were thereafter induced into the concrete pipe at predetermined inducing locations by impacting the inside diameter of the pipe with a Schmidt hammer manufactured by James Instruments of Chicago, Ill., and marketed as an "H-Meter." Shear waves were induced at six different annuli: (1) at an annulus located at the first end of the pipe, (2) at an annulus about four feet away from the first end, (3) at an annulus about 8 feet from the first end, (4) at an annulus about 12 feet away from the first end; (5) at an annulus about 16 feet away from the first end; and (6) at an annulus located at the second end of the pipe. Along each annulus, shear waves were induced at four separate locations: (a) at an uppermost position along the annulus (the "12 o'clock" position), (b) at a point along each annulus 90° from the uppermost point along one side of the concrete pipe (the "3 o'clock position"), (c) at a point along each annulus 180° from the uppermost point (the "6 o'clock" position) and (d) at a point 90° from the uppermost point along the opposite side of the concrete pipe (the "9 o'clock" position).

Data from each shear wave inducement was gathered by the acoustic sensors and stored and processed in a PC computer using software sold by Physical Acoustics of Lawrenceville, N.J., marketed as "MISTRAS."

After shear waves were induced at each of the four inducing locations along each of the six annuli, the computer program calculated various parameters from data received from the two acoustic sensors and printed out graphical representations of those parameters. Those graphical representations are shown in FIGS. 3 and 4. FIG. 3 graphically illustrates three parameters: energy, total counts and duration. FIG. 4 graphically illustrates three additional parameters of the received shear wave data: rise time, counts-to-peak and frequency.

In both FIGS. 3 and 4, that portion of each curve between −10 and −5 represents data received along the entire length of the pipe from shear waves induced along each of the uppermost points (at the 12 o'clock position) on the annuli. That portion of each curve between −5 and −1 represents data received along the entire length of the pipe from shear waves induced at each of the annuli at the 3 o'clock position. That portion of each curve between −1 and +5 represents data received along the length of the pipe at annulus locations at the 6 o'clock position on each annulus. Finally, that portion of each curve between +5 and +10 illustrates the data received along those points at each annulus located at the 9 o'clock position on each annulus.

The data used to prepare FIGS. 3 and 4 was analyzed by a technician. The technician noted U-shaped curves for all data received between points −10 and −5, −5 and −1 and −1 and +5. The technician interpreted these results as indicative that no integrity defects existed along the 12 o'clock, 3 o'clock and 6 o'clock positions. This is because experiments have found that data taken along a single elevation shows a generally U-shaped curve. This is believed due to the fact that the combined amplitude of each of the major parameters received at the two acoustic sensors is highest proximate to one of the acoustic sensors and is lowest (through dampening within the pipe) at inducing locations near the middle of the pipe—locations distal from either of the two acoustic sensors.

Discontinuities, however, generally interfere with the natural dampening effects along the length of the pipe. This means that, where a defect exists at a certain location along the length of the pipe and at a certain elevation along the pipe wall, data taken along that elevation will reveal a non-U-shaped curve. This is what is revealed in FIGS. 3 and 4 from data gathered along the 9 o'clock position (between +5 and +10). In all of the data, there is a distinctive intermediate peak at +7. This indicates that something within the pipe—probably a discontinuity—is interfering with the natural dampening of shear waves within the pipe. From the data illustrated in FIGS. 3 and 4, this discontinuity can be pinpointed at a position slightly less than half way between the first end and the second end and at an elevation close to the 9 o'clock position on the pipe.

In the present example, the mortar layer on the pipe was removed at the indicated location of the discontinuity and a break in the stress wire was noted.

Accordingly, this example illustrates that a section of pipe can be quickly, easily and inexpensively tested for integrity, without doing any structural damage to the pipe itself. Not only can the test procedure of the invention identify pipe sections having discontinuities, but the test procedure of the invention can pinpoint where that discontinuity is located.

Having thus described the invention, it should be apparent that numerous structural modifications and adaptations may be resorted to without departing from the scope and fair meaning of the instant invention as set forth hereinabove and as described hereinbelow by the claims.

It is claimed:

1. A method for testing a prestressed concrete conduit which comprises a hollow concrete body tightly wrapped with a prestressing wire, the method comprising the steps of:
   (a) serially inducing an elastic wave having a shear wave component into the conduit at at least three different inducing locations along the surface of the conduit;
   (b) sensing each shear wave component induced at each of the inducing locations with at least one acoustic sensor disposed at a first fixed sensing site proximate to the conduit;
   (c) correlating the relationship between (i) at least one parameter of each shear wave component induced at each inducing location and sensed by the acoustic sensor, and (ii) and the distance between said each inducing location and the acoustic sensor; and
   (d) comparing the correlations produced in step (c) with a standard correlation to identify structural discontinuities in the conduit.

2. The method of claim 1 wherein the concrete body has a first end and a second end and wherein at least three of the at least three inducing locations are at different distances $d_1$, $d_2$ and $d_3$ from such first end of the concrete body.

3. The method of claim 2 wherein at least two of the at least three inducing locations are at each of the three distances $d_1$, $d_2$ and $d_3$ from the first end of the concrete body.

4. The method of claim 2 wherein $d_1$, $d_2$ and $d_3$ are all between about 2' and 4'.

5. The method of claim 2 wherein at least one of the at least three inducing locations are at each of the three distances $d_1$, $d_2$ and $d_3$ from the first end of the concrete body.

6. The method of claim 2 wherein the distance between adjoining inducing locations disposed $d_1$ from the first end of the concrete body are substantially equal, the distance between adjoining inducing locations disposed $d_2$ from the first end of the concrete body are substantially equal and the distance between adjoining inducing locations disposed $d_3$ from the first end of the concrete body are substantially equal.

7. The method of claim 2 wherein $d_1$ is substantially equal to $d_2$ and $d_3$.

8. The method of claim 1 wherein said at least one sensor in step (b) comprises a first acoustic sensor disposed at the first fixed sensing site proximate to the conduit and by a second acoustic sensor disposed at a second fixed sensing site proximate to the conduit, and wherein the correlating step of step (c) correlates the relationship between (i) at least one parameter of each shear wave component induced at each inducing location and sensed by the acoustic sensors, and (ii) a distance parameter which is mathematically related to each combined distance between each inducing location and each of the acoustic sensors.

9. The method of claim 1 wherein the hollow concrete body comprises an interior wall and wherein the elastic wave is induced into the conduit in step (a) at inducing locations along the surface of the interior wall.

10. The method of claim 1 wherein the pre-stressing wire is covered with a filler material to form an exterior wall and wherein the elastic wave is induced into the conduit in step (a) at inducing locations along the surface of the exterior wall.

11. The method of claim 9 wherein the shear wave component of the elastic wave is sensed in step (b) at a fixed sensing site proximate to the interior wall.

12. The method of claim 1 wherein the correlating step of step (c) requires correlating the relationship between at least three parameters of the shear wave component sensed by the acoustic sensor from each inducing location (ii) and the distance between said each inducing location and the first fixed sensing site.

13. The method of claim 1 wherein the correlating step of step (c) requires correlating the relationship between more than three parameters of the shear wave component sensed by the acoustic sensor from at each inducing location (ii) and the distance between said each inducing location and the first fixed sensing site.

14. The method of claim 10 wherein the shear wave component of the elastic wave is sensed in step (b) at a fixed sensing site proximate to the exterior wall.

15. The method of claim 8 wherein the concrete conduit has a first end and a second end and wherein the first acoustic sensor is disposed proximate to the first end and the second acoustic sensor is disposed proximate to the second end.

16. The method of claim 1 wherein the concrete conduit is a conduit section which is connected end-to-end with at least one other conduit section to form a concrete conduit network.

17. The method of claim 1 wherein the parameter of the shear wave component which is correlated in step (c) is the energy of the shear wave component.

18. The method of claim 1 wherein the parameter of the shear wave component which is correlated in step (c) is the amplitude of the shear wave component.

19. The method of claim 1 wherein the parameter of the shear wave component which is correlated in step (c) is the frequency of the shear wave component.

20. The method of claim 1 wherein the parameter of the shear wave component which is correlated in step (c) is the counts above a predetermined threshold of the shear wave component.

21. The method of claim 1 wherein the parameter of the shear wave component which is correlated in step (c) is the duration of the shear wave component.

22. The method of claim 1 wherein the parameter of the shear wave component which is correlated in step (c) is the average frequency of the shear wave component.

23. The method of claim 1 wherein the parameter of the shear wave component which is correlated in step (c) is the rise time of the shear wave component.

24. The method of claim 1 wherein the parameter of the shear wave component which is correlated in step (c) is the velocity of the shear wave component.

25. The method of claim 1 wherein the parameter of the shear wave component which is correlated in step (c) is the counts to peak of the shear wave component.

26. The method of claim 1 wherein the correlating step of step (c) requires correlating the relationship between at least two parameters of the shear wave component sensed by the acoustic sensor from each inducing location (ii) and the distance between said each inducing location and the first fixed sensing site.

27. The method of claim 12 wherein the parameters of the shear wave component which is correlated in step (c) is the amplitude, the average frequency and the counts of the shear wave component.

28. The method of claim 12 wherein the parameters of the shear wave component which is correlated in step (c) is the amplitude, the velocity and the frequency of the shear wave component.

29. The method of claim 26 wherein the parameters of the shear wave component which is correlated in step (c) is the energy and the amplitude of the shear wave component.

30. The method of claim 26 wherein the parameters of the shear wave component which is correlated in step (c) is the amplitude and the average frequency of the shear wave component.

31. The method of claim 26 wherein the parameters of the shear wave component which is correlated in step (c) is the amplitude and the counts of the shear wave component.

32. The method of claim 26 wherein the parameters of the shear wave component which is correlated in step (c) is the velocity and the frequency of the shear wave component.

33. The method of claim 27 wherein the parameters of the shear wave component which is correlated in step (c) is the energy, the amplitude and the counts of the shear wave component.

34. The method of claim 27 wherein the parameters of the shear wave component which is correlated in step (c) is the energy, the average frequency and the counts of the shear wave component.

35. A method for testing a prestressed concrete conduit which comprises a round, hollow concrete body having a first end and a second end and being tightly wrapped with a prestressing wire, the method comprising the steps of:

(a) serially inducing an elastic wave having a shear wave component into the conduit at at least three different inducing locations along the surface of the conduit wherein at least three of the inducing locations are at different distances $d_1$, $d_2$ and $d_3$ from such first end of the concrete body;

(b) sensing each shear wave component induced at each inducing location by a first acoustic sensor disposed at a first fixed sensing site proximate to the first end of the concrete body and in physical contact with the conduit and by a second acoustic sensor disposed at a second fixed sensing site proximate to the second end of the concrete body and in physical contact with the conduit;

(c) correlating the relationship between (i) at least one parameter of each shear wave component induced at each inducing location and sensed by the acoustic sensors, and (ii) and a distance parameter which is mathematically related to each combined distance between each inducing location and each of the acoustic sensors; and (d) comparing the correlations produced in step (c) with a standard correlation to identify structural discontinuities in the conduit.

36. The method of claim 35 wherein at least two of the at least three inducing locations are at each of the three distances $d_1$, $d_2$ and $d_3$ from the first end of the concrete body.

37. The method of claim 35 wherein $d_1$, $d_2$ and $d_3$ are all between about 2' and 4'.

38. The method of claim 35 wherein at least three of the at least three inducing locations are at each of the three distances $d_1$, $d_2$ and $d_3$ from the first end of the concrete body.

39. The method of claim 35 wherein the distance between adjoining inducing locations disposed $d_1$ from the first end of the concrete body are substantially equal, the distance between adjoining inducing locations disposed $d_2$ from the first end of the concrete body are substantially equal and the distance between adjoining inducing locations disposed $d_3$ from the first end of the concrete body are substantially equal.

* * * * *